(12) United States Patent
Silcott et al.

(10) Patent No.: US 10,209,184 B2
(45) Date of Patent: Feb. 19, 2019

(54) REMOVABLE INSERT FOR A TEST UNIT HAVING A LIGHT SOURCE FOR ILLUMINATING AN AEROSOL TEST CHAMBER

(71) Applicant: HAMILTON ASSOCIATES, INC., Owings Mills, MD (US)

(72) Inventors: David B. Silcott, Reisterstown, MD (US); Brian Bolton, Columbia, MD (US)

(73) Assignee: HAMILTON ASSOCIATES, INC., Owings Mills, MD (US)

( * ) Notice: Subject to any disclaimer, the term of this patent is extended or adjusted under 35 U.S.C. 154(b) by 311 days.

(21) Appl. No.: 15/095,271

(22) Filed: Apr. 11, 2016

(65) Prior Publication Data

US 2017/0292910 A1 Oct. 12, 2017

(51) Int. Cl.
*G01N 21/51* (2006.01)

(52) U.S. Cl.
CPC ..... *G01N 21/51* (2013.01); *G01N 2201/06113* (2013.01)

(58) Field of Classification Search
CPC ............ G01N 21/51–21/538; G01N 2021/513
See application file for complete search history.

(56) References Cited

U.S. PATENT DOCUMENTS

| 8,125,626 | B2 * | 2/2012 | Furtaw | G01N 21/3504 356/437 |
|---|---|---|---|---|
| 8,520,205 | B2 | 8/2013 | Silcott et al. | |
| 8,539,840 | B2 | 9/2013 | Ariessohn et al. | |
| 9,304,117 | B2 | 4/2016 | Rodes et al. | |
| 2006/0246594 | A1 * | 11/2006 | Appel | G01N 21/6408 436/81 |
| 2014/0347663 | A1 | 11/2014 | Rodes et al. | |
| 2015/0369706 | A1 | 12/2015 | Miller | |

FOREIGN PATENT DOCUMENTS

| EP | 2679985 | 1/2014 |
|---|---|---|
| WO | WO 2016028997 | 2/2016 |

OTHER PUBLICATIONS

International Search Report dated Jun. 8, 2017 issued in connection with PCT/US2017/026766, 2 pages (NPL1).
Written Opinion dated Jun. 28, 2017 in connection with PCT/US2017/026766, 10 pages (NPL2).

* cited by examiner

*Primary Examiner* — Tri T Ton
*Assistant Examiner* — Rebecca C Bryant
(74) *Attorney, Agent, or Firm* — Merek, Blackmon & Voorhees, LLC

(57) ABSTRACT

A test unit having a light source (e.g., a laser) for illuminating an aerosol sample directed into a test chamber and a removable insert for the test unit. The test unit includes at least one detector for detecting the effect of the aerosol sample on light, i.e., the detector detects at least one property of light after the light has illuminated the aerosol sample. The removable insert may take a number of different forms. For example, the removable insert can form at least a portion of an unsealed or sealed test chamber when installed in an operating position. Further, the removable insert may include a removable support and at least one film or collection substance connected or applied to the removable support. The at least one film could be a filter or a non-filter. The filter could be a polarization filter (i.e., horizontal or vertical) or a fluorescence filter.

19 Claims, 7 Drawing Sheets

Figure 1:
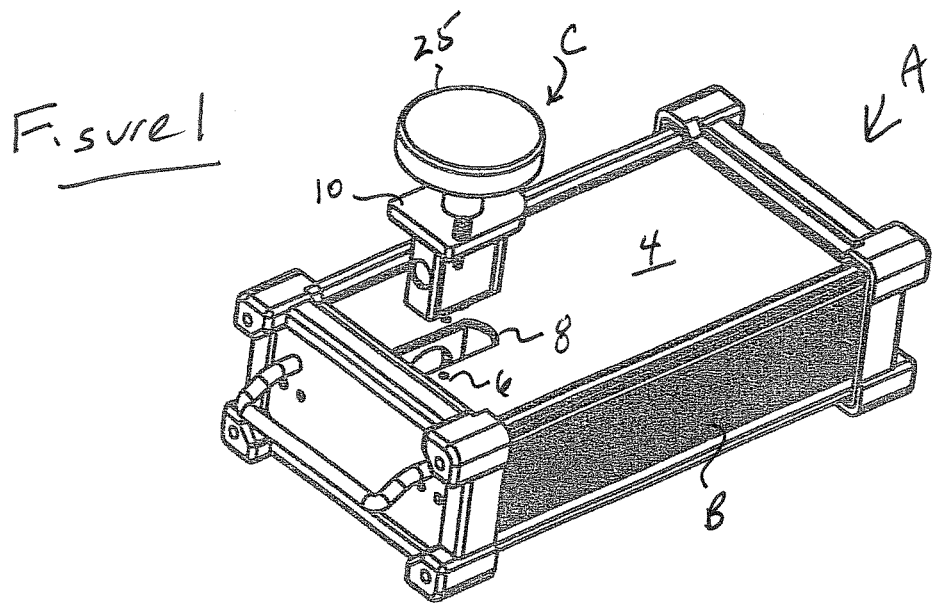
Figure 2:
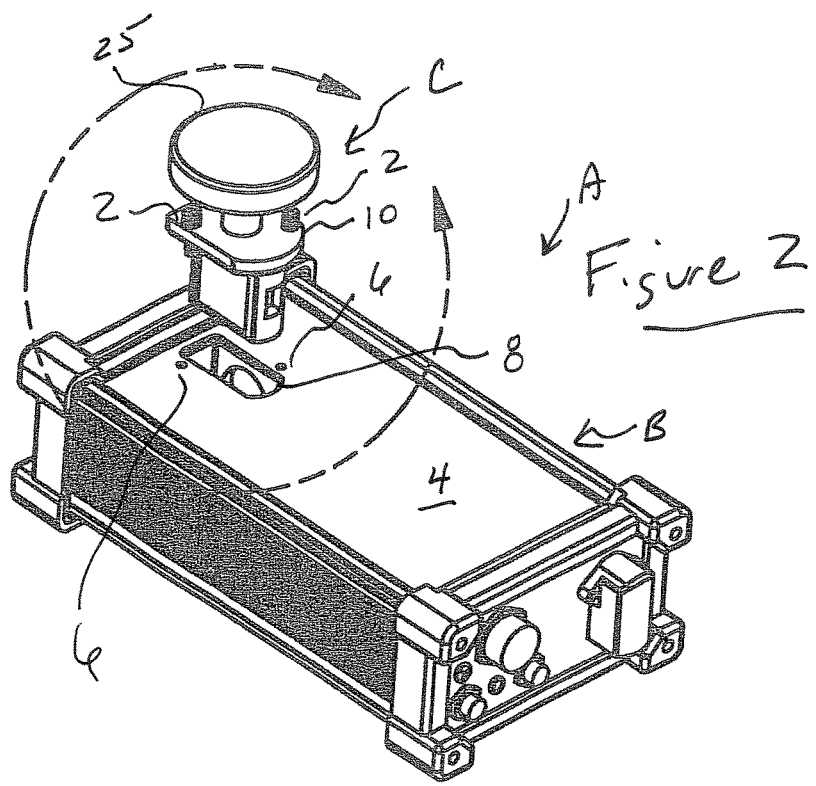
Figure 3:
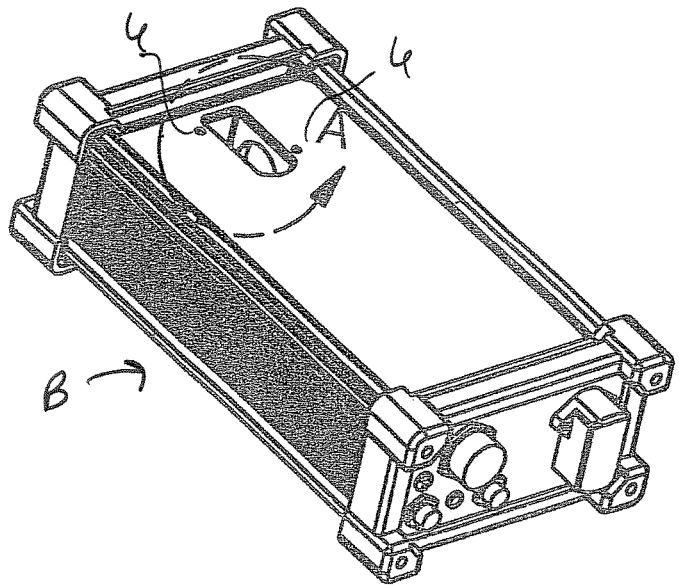
Figure 4:
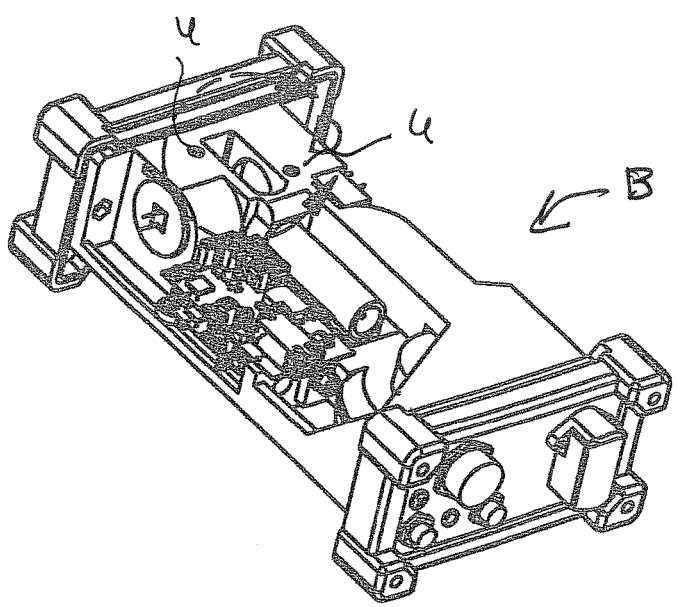
Figure 5:
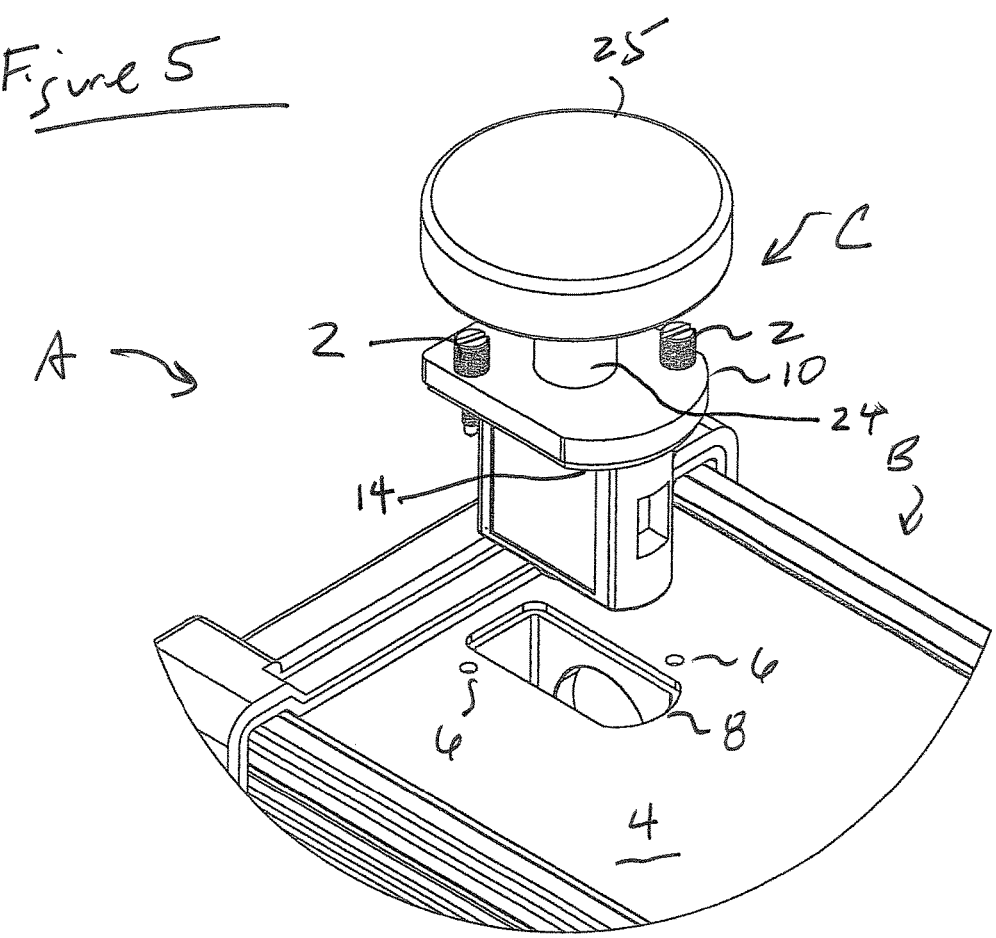

REMOVABLE INSERT FOR A TEST UNIT HAVING A LIGHT SOURCE FOR ILLUMINATING AN AEROSOL TEST CHAMBER

FIELD OF THE INVENTION

A preferred form of the present invention is directed to a test unit having a light source (e.g., a laser) for illuminating an aerosol sample directed into an aerosol test chamber and a removable insert for the test unit. The test unit includes at least one detector for detecting the effect of the aerosol sample on the light, i.e., the detector detects at least one property of light after the light has illuminated the aerosol sample.

The removable insert may take a number of different forms. For example, the removable insert can form at least a portion of an unsealed aerosol test chamber when installed in an operating position in the test unit. Alternatively, the removable insert can form a sealed aerosol test chamber when installed in an operating position in the test unit. Further, the removable insert may include a removable support and at least one film connected to the removable support such that the removable support and at least one film are inserted into and removed from the test unit together. The at least one film could be a filter or a non-filter. The at least one film could be a collection layer or collection substance applied to the at least one support that collects particles from the aerosol sample. The filter could be a polarization filter (i.e., horizontal or vertical) or a fluorescence filter.

BACKGROUND OF THE INVENTION

Optical test units that sense light scatter resulting from a fluid test sample (e.g., an aerosol test sample) being illuminated by light generated by a light source (e.g., laser) are known. Known optical test units include photometers, biological detectors, particle counters and dust monitors. However, known optical test units have a number of limitations and/or disadvantages. Preferred forms of the present invention have been developed to significantly reduce the limitations and/or overcome one or more disadvantages of known optical test units.

OBJECTS AND SUMMARY OF THE INVENTION

An object of the present invention is to provide a novel and unobvious test unit assembly sensing light scatter resulting from illumination of a test sample (e.g. an aerosol test sample) by light generated by a light source (e.g., a laser).

An object of the present invention is to provide a novel and unobvious removable insert for a test unit sensing light scatter resulting from illumination of a test sample (e.g. an aerosol test sample) by light generated by a light source (e.g., a laser).

Another object of a preferred embodiment of the present invention is to provide a removable insert for an optical test unit that when installed in the optical test unit forms a sealed test chamber to prevent contamination of one or more components of the optical test unit.

A further object of a preferred embodiment of the present invention is to provide an insert for an optical test unit that can be readily and easily removed from and connected to the optical test unit.

Yet another object of a preferred embodiment of the present invention is to provide a removable insert for a test unit where the insert includes at least one filter that filters light prior to light illuminating a test sample to allow the at least one filter to be readily and easily inserted into and removed from an operating position in the test unit.

Still a further object of a preferred embodiment of the present invention is to provide a removable insert for a test unit where the insert includes at least one filter that filters light after light illuminates a test sample to allow the at least one filter to be readily and easily inserted into and removed from an operating position in the test unit.

Still another object of a preferred embodiment of the present invention is to provide a removable insert for a test unit where the insert includes a particle collecting member or substance to trap at least some particles of the test sample where the insert with the trapped particles can be readily removed from the test unit so that the trapped particles can be processed or otherwise analyzed.

Yet still another object of a preferred embodiment of the present invention is to provide a removable insert for a test unit that can be readily and easily installed in and removed from an operating position without removing the outer shell/housing of the test unit.

Still a further object of a preferred embodiment the present invention is to provide a removable insert that allows an individual to readily and easily alter, change or otherwise modify at least one characteristic of an optical test unit.

A further object of a preferred embodiment of the present invention is to provide an optical test assembly having an optical test unit that can receive a number of different removable inserts to allow an individual to readily and easily alter, change or otherwise modify at least one characteristic of an optical test unit by replacing one removable insert with a different removable insert.

It must be understood that no one embodiment of the present invention need include all of the aforementioned objects. Rather, a given embodiment may include one or none of the aforementioned objects. Accordingly, these objects are not to be used to limit the scope of the claims of the present invention.

In summary, one embodiment of the present invention is directed to a removable aerosol test chamber configured to be inserted into and removed from an optical test unit having optical components including a light source for illuminating an aerosol sample directed into the removable aerosol test chamber and at least one detector for detecting at least one characteristic of light illuminating the aerosol sample directed into the removable aerosol test chamber. The removable aerosol test chamber includes a housing having an aerosol test chamber, an aerosol inlet and a light inlet. The aerosol inlet of the housing is configured to introduce an aerosol sample into the aerosol test chamber. The light inlet is configured to direct light from a light source into the aerosol test chamber when the removable aerosol test chamber is installed in an optical test unit in an operating position. The removable aerosol test chamber is configured to isolate an aerosol sample passing through the aerosol test chamber from at least one optical component of the optical test unit to prevent the at least one optical component from becoming contaminated by the aerosol sample.

Another embodiment of the present invention is directed to a removable aerosol test chamber configured to be inserted into and removed from an optical test unit having optical components including a light source for illuminating an aerosol sample directed into the removable aerosol test chamber and at least one detector for detecting at least one characteristic of light illuminating the aerosol sample directed into the removable aerosol test chamber. The removable aerosol test chamber includes a removable housing having an aerosol test chamber, an aerosol inlet and a light inlet. The aerosol inlet of the removable housing is configured to introduce an aerosol sample into the aerosol test chamber. The light inlet is configured to direct light from a light source into the aerosol test chamber when the removable aerosol test chamber is installed in an optical test unit in an operating position. At least one film is connected to the removable housing. The film is disposed such that at least a first portion of light illuminating the aerosol sample will pass through the at least one film before the first portion of light is detected by the at least one detector. The at least one film is connected to the removable housing such that the at least one film is removed from the optical test unit with the removable housing.

A further embodiment of the present invention is directed to a removable aerosol test chamber configured to be inserted into and removed from an optical test unit having optical components including a light source for illuminating an aerosol sample directed into the removable aerosol test chamber and at least one detector for detecting at least one characteristic of light illuminating the aerosol sample directed into the removable aerosol test chamber. The removable aerosol test chamber includes a removable housing having an aerosol test chamber, an aerosol inlet and a light inlet. The aerosol inlet of the removable housing is configured to introduce an aerosol sample into the aerosol test chamber. The light inlet is configured to direct light from a light source into the aerosol test chamber when the removable aerosol test chamber is installed in an optical test unit in an operating position. The removable housing further includes a particle collector for collecting particles from the aerosol sample passing into the aerosol test chamber such that upon removal of the removable housing from the optical test unit particles collected on the particle collector remain in the removable housing.

Still a further embodiment of the present invention is directed to a removable insert configured to be inserted into and removed from a test unit having a light source for illuminating an aerosol sample directed into an aerosol test chamber and at least one detector for detecting at least one characteristic of light illuminating the aerosol sample directed into the aerosol test chamber. The removable insert includes a removable support configured to be inserted into and removed from the test unit. The removable insert further includes at least one of the following: (i) at least one film, the at least one film is connected to the removable support such that the at least one film is removed from the test unit with the removable support, the at least one film is disposed such that at least a first portion of light from the light source will pass through the at least one film before the first portion of light is detected by at least one detector of the test unit; and, (ii) a particle collection means for collecting particles from the aerosol sample, the particle collection means is operably associated with the removable support such that particles collected by the particle collection means are removed from the test unit upon removal of the removable support from the test unit.

The above summary describes preferred forms of the present invention and is not in any way to be construed as limiting the claimed invention to the preferred forms.

BRIEF DESCRIPTION OF THE DRAWINGS

FIG. 1 is an exploded perspective view of a test unit having a removable insert formed in accordance with a preferred embodiment of the present invention.

FIG. 2 is an exploded perspective view of the test unit and removable insert of FIG. 1 taken from a different vantage point.

FIG. 3 is a perspective view of the test unit of FIG. 1.

FIG. 4 is a partial sectional view of the test unit of FIG. 1 with the outer shell/housing removed.

FIG. 5 is a detail view of the portion encompassed by the circular dashed lines A in FIG. 1.

FIG. 6 is a detail view of the portion encompassed by the circular dashed lines A in FIG. 3.

FIG. 7 is a detail view of the portion encompassed by the circular dashed lines D in FIG. 4.

FIG. 8 is a detail view of a portion of the test unit encompassed by the circular dashed lines D in FIG. 4 with the collecting lens shown removed from the test unit.

FIG. 9 is an enlarged exploded perspective view of a removable insert formed in accordance with a preferred embodiment of the present invention with portions thereof removed.

FIG. 10 is an enlarged exploded perspective view of the removable insert depicted in FIG. 9.

FIG. 11 is an enlarged sectional view of the removable insert depicted in FIG. 9 with portions of the removable insert omitted (i.e., not shown).

FIG. 12 is an enlarged perspective view of the removable insert depicted in FIG. 9 with portions of the removable insert omitted (i.e., not shown).

FIG. 13 is an enlarged perspective view of the removable insert depicted in FIG. 9 with portions of the removable insert omitted (i.e., not shown).

FIG. 14 is an enlarged exploded perspective view of a removable insert formed in accordance with another preferred embodiment of the present invention with portions thereof removed.

FIG. 15 is an enlarged perspective view of the removable insert formed in accordance with embodiment depicted in FIG. 14 with portions thereof removed.

FIG. 16 is an enlarged perspective view of the removable insert formed in accordance with embodiment depicted in FIG. 14 with portions thereof removed.

DETAILED DESCRIPTION OF THE PREFERRED EMBODIMENTS OF THE INVENTION

The preferred forms of the test unit assembly will now be described with reference to FIGS. 1-16. The appended claims are not limited to the preferred forms and no term and/or phrase used herein is to be given a meaning other than its ordinary meaning unless it is expressly stated otherwise.

FIGS. 1 Through 13

Referring to FIGS. 1 to 8, a preferred form of test unit assembly A is illustrated in one of many possible configurations. The test unit assembly A includes a base test unit B and a removable insert C. The test unit B is preferably an optical test unit that directs light from a light source (e.g., a laser) to a test chamber to illuminate a fluid sample (e.g., aerosol sample). Test unit B includes at least one detector for detecting the effect of the aerosol sample on the light, i.e., the detector detects at least one property of light after the light has illuminated the aerosol sample. For example, the at least one detector can detect light scatter caused by the aerosol sample.

Test unit B may include a single detector detecting light scatter exiting one side of removable insert C. Alternatively, test unit B may include two or more detectors detecting light scatter exiting one side of removable insert C. Further, test unit B may include two detectors where one detector detects light scatter exiting a first side of removable insert C and the other detector detects light scatter exiting a second side (e.g., a side opposite of the first side) of removable insert C. For each detector, test unit B may include an amplifier followed by an analog/digital convertor where the amplifier and analog/digital convertor act on the signal generated by the corresponding detector. Test unit B may include a microprocessor for processing the signal generated by the analog/digital convertor. The microprocessor may be external to test unit B.

The test unit B may include a vacuum pump to pull the fluid sample through the test chamber and discharge the same from an exit portion of the test unit B. Alternatively, the test unit B may be connected to an external vacuum source to pull the fluid sample through the test chamber. The light source can be any suitable light source. Typically, the light source will be housed in the test unit B but such is not required to implement the present invention. Examples of suitable light sources include but are not limited to an edge emitting laser diode, a vertical cavity surface emitting laser diode, a light emitting diode or other laser source. Further, the light source is not limited to laser type light sources. Rather, any suitable light source can be used including non-laser type light sources.

Test unit B can take many forms including an aerosol biological detector, a particle counter, a dust monitor, or a photometer. Test unit B may include a number of optical components acting on the light generated by the light source prior to the light entering the test chamber. For example, the optical components in test unit B may include an aspheric lens which collimates light generated by the light source followed by beam shaping optics, a linear polarization filter, a quarter wave retarder and a bire fringement crystal. This is just one example of the optical components that may act on light prior to light entering the test chamber. The number and type of optical components acting on light prior to entry in the test chamber may be readily varied as desired. Test unit B may include a number of optical components acting on the light exiting the test chamber prior to entering a light detector. These optical components may include a filter followed by collection optics (e.g., collection lens). The filter could be a fluorescence filter, a horizontal depolarization filter or a vertical depolarization filter.

Referring to FIGS. 5 and 9 to 13, two fasteners 2 detachably connect removable insert C to test unit B. Preferably, insert C and test unit B are configured such that insert C can be connected to and detached from test unit B without removing outer shell or housing 4 of test unit B. Preferably, fasteners 2 are threaded to mate with a corresponding threaded bore 6 in test unit B. While two fasteners 2 are shown, the number of fasteners may be readily varied as desired. Further, while fasteners 2 are shown as being screws, any type of fastener may be used to connect insert C to test unit B.

When connected to test unit B, the lower portion of insert C extends into opening 8 of outer shell 4 such that the lower surface 12 of cover 10 of insert C is disposed directly adjacent and/or in contact with outer shell 4. A seal may be provided between lower surface 12 and the adjacent area of outer shell 4 to prevent undesired matter from entering test unit B through opening 8. Alignment member or skirt 14 extends downwardly from lower surface 12 and extends into opening 8 to orient insert C relative to the test unit B during installation of insert C. Alignment member or skirt 14 is preferably configured similar to opening 8 and is slightly smaller than opening 8. It should be understood that the configuration of alignment member 14 and opening 8 may be readily varied as desired. Further, alignment member 14 could be omitted as fasteners 2 can be used as the sole alignment means for orienting insert C relative to test unit B.

Figure 8:
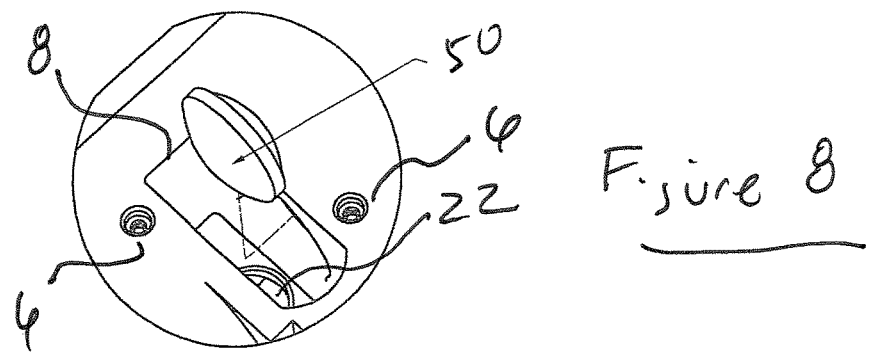
Figure 9:
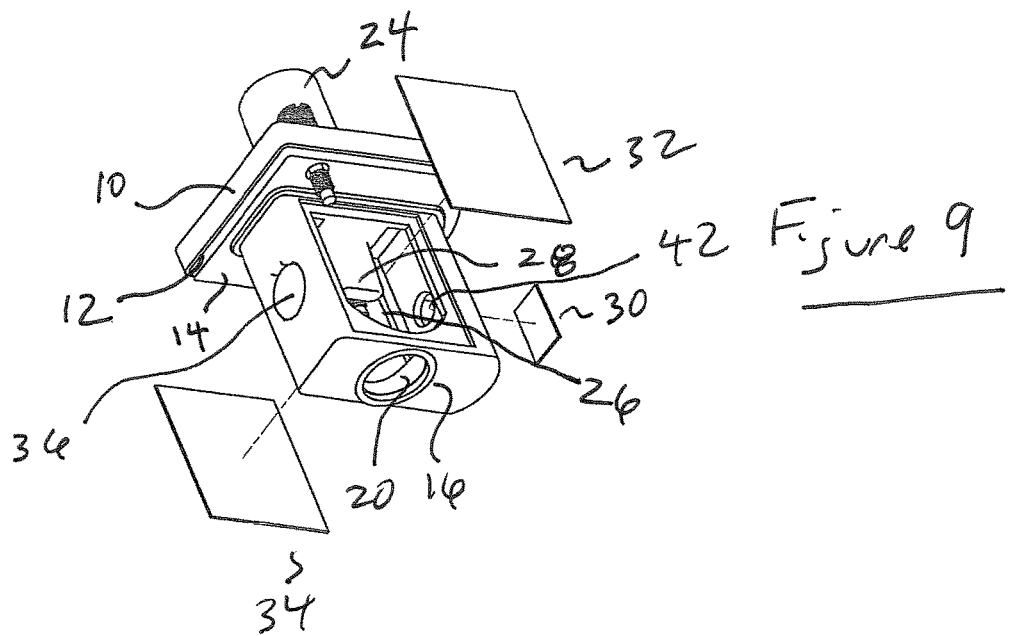
Figure 10:
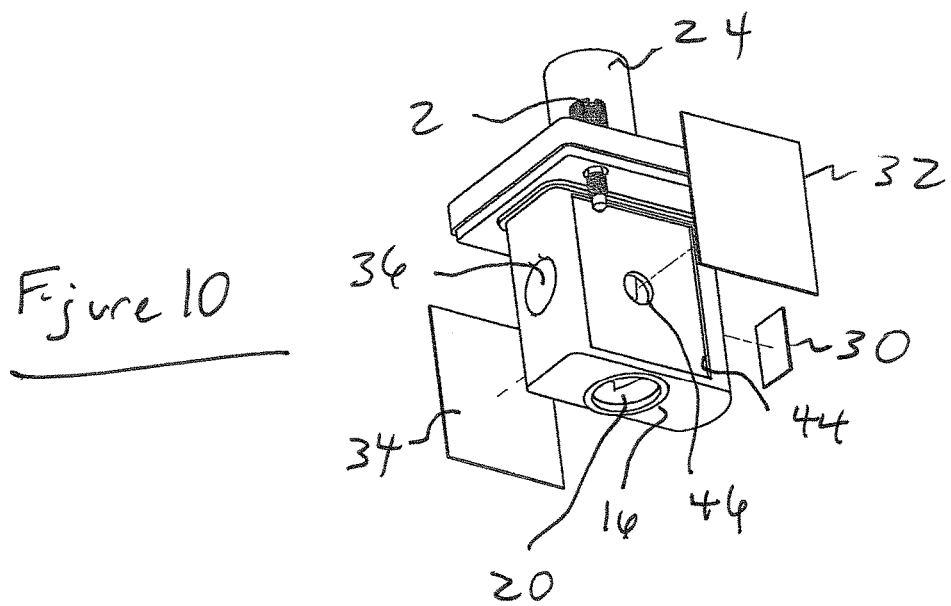
Figure 11:
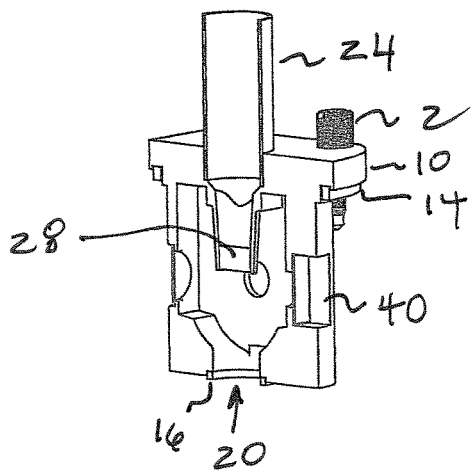
Figure 12:
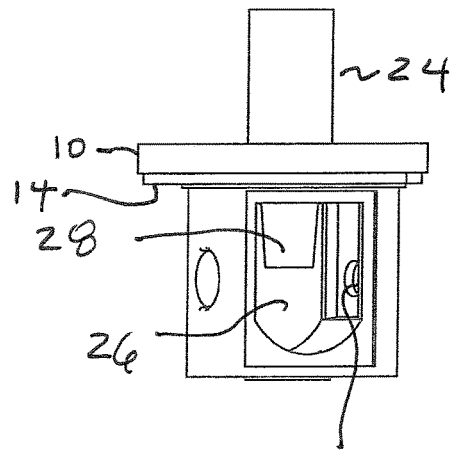
Figure 13:
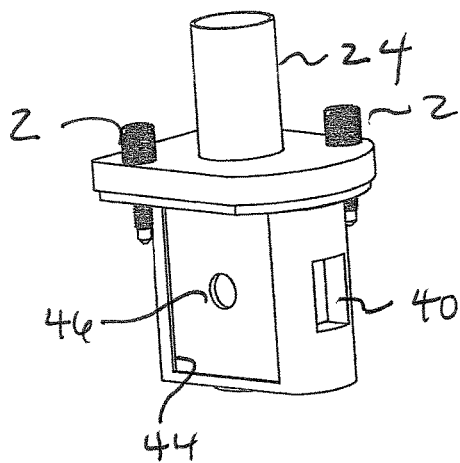

Referring to FIGS. 8 to 10, insert C may include a seal 16 for sealing the connection of lower exit port 20 of insert C and port 22 of the vacuum line or conduit (not shown) of test unit B. Insert C includes a tubular conduit 24. An aerosol inlet also known as a rain cap 25 is in fluid communication with tubular conduit 24. Tubular conduit 24 directs an aerosol sample pulled through rain cap 25 by a vacuum source into test chamber 26 formed by insert C. In this manner test unit B can test in-situ the quality and/or one or more characteristics of air in the environment where the test unit B is located.

The lower portion of tubular conduit 24 may include a nozzle 28 which directly communicates with test chamber 26. It should be noted that tubular conduit 24 and nozzle 28 could be formed from a single piece. Alternatively, tubular conduit 24 and nozzle 28 could be separate pieces.

Referring to FIGS. 9 and 10, insert C includes films 30, 32, 34 and light trap 36. Films 30, 32 and 34 may be filters or non-filters. Preferably, films 30, 32, 34 are configured to allow light to pass therethrough. Films 30, 32 and 34 are preferably attached to insert C in a sealed tight manner to seal the corresponding portions of insert C. Hence, films 30, 32, 34 and seal 16 form a sealed test chamber 26. Sealed test chamber 26 prevents contamination of the internal components of test unit B including but not limited to the optical components of test unit B. Light trap 36 traps light to prevent backscatter of light in test chamber 26. While the preferred embodiment includes a sealed test chamber 26, the test chamber could be unsealed. Further, the insert C need not include a test chamber. For example, insert C could include one or more removable supports for supporting one or more of films 30, 32 and 34 detachably connected to test unit B to allow for the removal and replacement of one or more of films 30, 32 and 34. An example of one possible removable support is an optically transparent support (e.g., a glass window).

Referring to FIGS. 9 to 12, insert C includes a rectangular recess 40 for receiving film 30 such that film 30 covers circular aperture 42. It should be appreciated that the shape of recess 40, film 30 and aperture 42 can be readily varied as desired. In a most preferred form of the invention, film 30 is a linear polarization filter (e.g., horizontal or vertical polarization filter). Insert C includes a rectangular recess 44 for receiving film 32 such that film 32 covers circular aperture 46. It should be appreciated that the shape of recess 44, film 32 and aperture 46 can be readily varied as desired. In a most preferred form of the invention, film 32 is a filter. The filter could be a horizontal depolarization filter, a vertical depolarization filter, a fluorescence filter or other suitable filter. Insert C includes a rectangular recess similar or identical to recess 44 for receiving film 34 such that film 34 covers a circular aperture similar or identical to aperture 46. In a most preferred form of the invention, film 34 is a filter. The filter could be a horizontal depolarization filter, a vertical depolarization filter, a fluorescence filter or other suitable filter. It should be noted that insert C may omit one of films 32 and 34. For example, if film 34 or film 32 is omitted, the corresponding side wall of insert C could be formed as a solid wall without any apertures.

Figure 6:
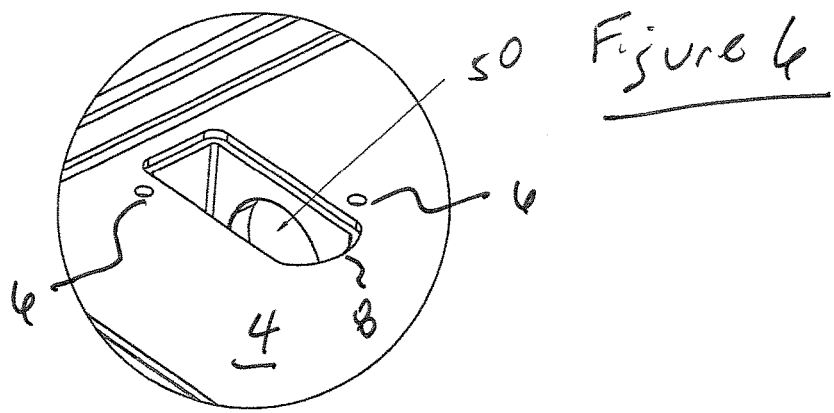
Figure 7:
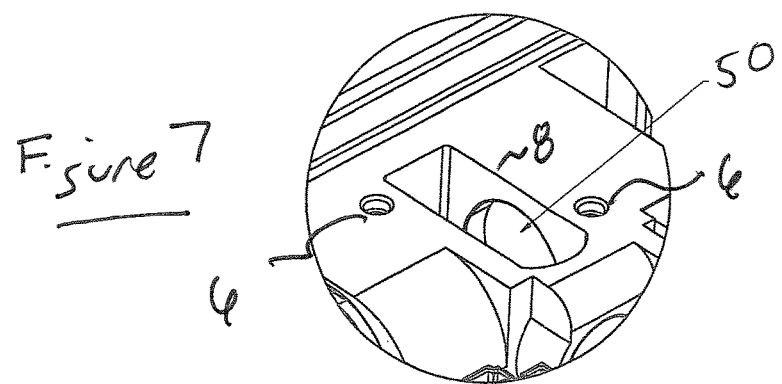

Referring to FIGS. 6 to 8, a collection lens 50 is shown as one optical component that will act on light passing through film 34 prior to traveling to the corresponding optical detector. A similar or identical collection lens to that of lens 50 may be oriented adjacent film 32.

Because the test unit B is configured to receive a removable insert, at least one characteristic of the test unit may be altered, changed or otherwise modified by merely removing an existing removable insert from the test unit B and replacing the same with a removable insert that differs in at least one respect from the previously removed insert. For example, an existing removable insert may form an unsealed test chamber when installed in test unit B. If the environment in which the test unit B is operating has changed to an environment where a sealed test chamber would be beneficial, the removable insert having an unsealed test chamber can be readily replaced with a removable insert that forms a sealed test chamber. Another example would be where the insert does not include a test chamber but rather is a removable support having one or more films operably connected thereto. By removing an existing removable insert and replacing it with another removable insert having at least one film that differs in function from the previously installed removable insert, one can readily change at least one characteristic of the optical test unit. For instances, if the installed removable insert had a single film functioning as a vertical depolarization filter, one could readily remove the installed removable insert and replace it with a filter functioning as a horizontal depolarization filter. Another example would be where an installed insert C is removed and replaced with insert D described below. In this instance, the test unit B is now able to collect particles from the test sample on or in insert D for subsequent processing or analysis.

Figure 14:
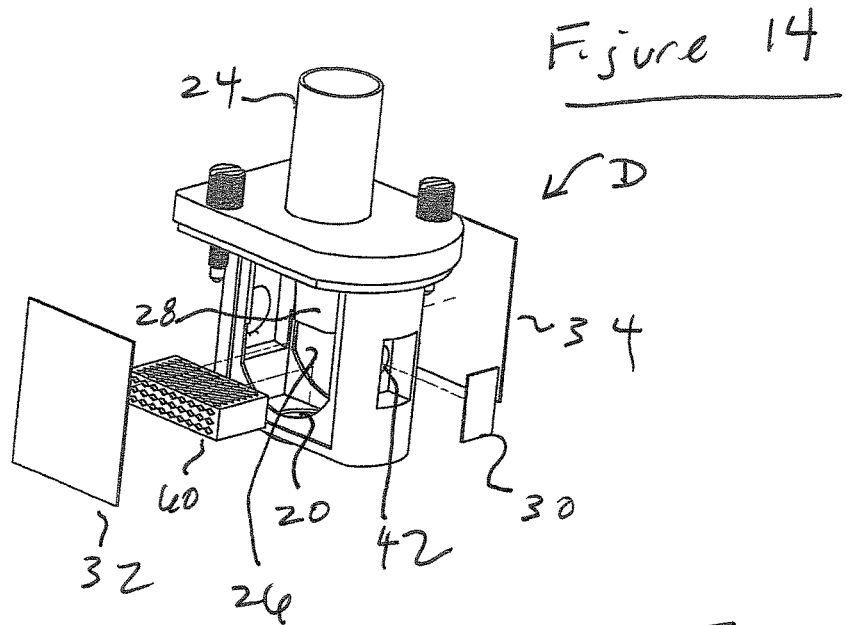
Figure 15:
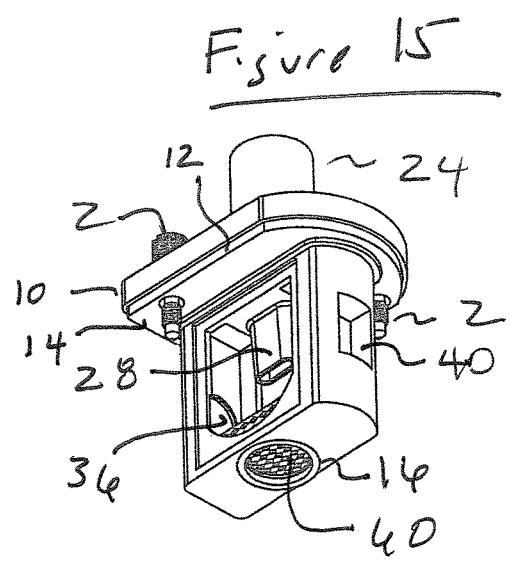
Figure 16:
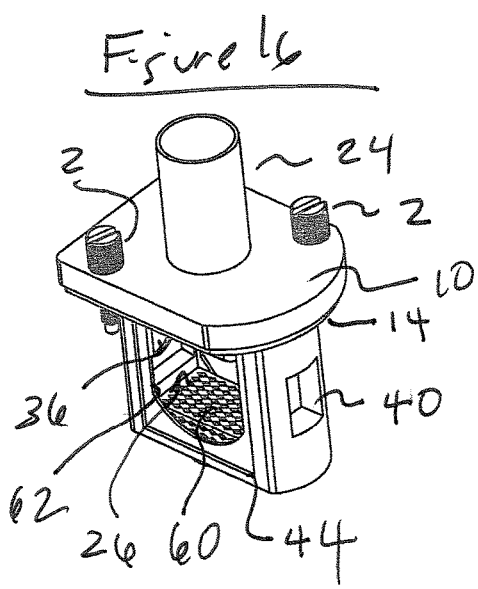

FIGS. 14 Through 16

Referring to FIGS. 14 to 16, an alternative form of removable insert D will be described. Removable insert D includes a number of features of removable insert C, therefore, only the differences will be discussed in detail. Further, all possible modifications of removable insert C discussed above are applicable to insert D. Use of the same reference numerals as those used in connection with insert C designate a feature of insert D that is the same as insert C.

The principle difference between insert D and insert C is the inclusion of particle collector 60 in insert D. Particle collector 60 is configured to allow air to be drawn through collector 60 while trapping particles in the fluid test sample that pass into test chamber 26. Particle collector 60 may be formed of felt-like filter media of the type used in DFU (Dry Filter Unit) collectors. Collector 60 is shown as a mesh cage which allows air to pass through the mesh cage while trapping particles from the fluid test sample. However, collector 60 may be pleated, layered or otherwise configured to provide more surface area for particle collection while allowing air to pass through the collector. As shown in FIGS. 14 to 16, a large opening 62 may be formed in one sidewall to allow for insertion of collector 60 into test chamber 26. The opposing sidewall of insert D could have an opening similar to opening 62. By providing insert D with collector 60, insert D can be readily removed from a corresponding test unit and the particles trapped by collector 60 can be further processed or analyzed. Insert D can be used with any suitable optical test unit including those previously described.

Collector 60 could be replaced with a tacky trapping substance applied to one or more surfaces (e.g., bottom surface) defining test chamber 26 that will act to collect particles in the fluid test sample passing into test chamber 26. Where the insert does not include a test chamber, the tacky trapping substance could be applied to one or more surfaces of a removable portion of the insert.

While this invention has been described as having a preferred design, it is understood that the preferred design can be further modified or adapted following in general the principles of the invention including but not limited to such departures from the present invention as come within the known or customary practice in the art to which the invention pertains. The claims are not limited to the preferred embodiments and have been written to preclude such a narrow construction using the principles of claim differentiation.

We claim:

1. A removable insert configured to be inserted into and removed from a housing of an optical test unit wherein the housing of the optical test unit houses one or more optical components including at least one of a light source for illuminating an aerosol sample directed into a removable aerosol test chamber and at least one detector for detecting at least one characteristic of light illuminating the aerosol sample directed into said removable aerosol test chamber, said removable insert comprising:
   (a) a removable insert housing having a removable aerosol test chamber, an aerosol inlet and a light inlet, said aerosol inlet of said removable insert housing being configured to introduce an aerosol sample into said removable aerosol test chamber, said light inlet being configured to direct light from a light source into said aerosol test chamber when said removable insert is installed in a housing of an optical test unit in an operating position, said removable insert being configured to isolate an aerosol sample passing through said removable aerosol test chamber from at least one optical component of the optical test unit to prevent the at least one optical component from becoming contaminated by the aerosol sample wherein said light inlet being configured to direct light in a path orthogonal to a path of an aerosol sample passing through the removable aerosol test chamber; and,
   (b) a sealing film for sealing at least a portion of said removable aerosol test chamber, said sealing film being connected to said removable insert housing such that said removable insert housing and said sealing film are removed from and inserted into said housing of said optical test unit as a single unit, said sealing film being a filter.

2. The removable insert of claim 1, further including:
   (a) at least one fastener for removably connecting said removable aerosol test chamber to the optical test unit.

3. The removable insert of claim 1, wherein:
   (a) said removable insert housing further includes an aerosol outlet configured to be connected to a vacuum generating source wherein the vacuum generating source causes the aerosol sample to be pulled through the aerosol test chamber in a path orthogonal to a path of light illuminating the aerosol sample and orthogonal to a path of light to at least one detector stored in the housing of the optical test unit.

4. The removable insert of claim 1, wherein:
   (a) said removable insert housing further includes a light trap for trapping light after the light illuminates the aerosol sample.

5. The removable insert of claim 1, wherein:
   (a) said removable insert housing is a removable cartridge.

6. A removable aerosol test chamber configured to be inserted into and removed from an optical test unit having optical components including a light source for illuminating an aerosol sample directed into said removable aerosol test chamber and at least one detector for detecting at least one characteristic of light illuminating the aerosol sample directed into said removable aerosol test chamber, said removable aerosol test chamber comprising:
   (a) a removable housing having an aerosol test chamber, an aerosol inlet and a light inlet, said aerosol inlet of said removable housing being configured to introduce an aerosol sample into said aerosol test chamber, said light inlet being configured to direct light from a light source into said aerosol test chamber when said removable aerosol test chamber is installed in an optical test unit in an operating position; and,
   (b) at least one film connected to said removable housing, said film be disposed such that at least a first portion of light illuminating the aerosol sample will pass through said at least one film before the first portion of light is detected by the at least one detector, said at least one film being connected to said removable housing such that said at least one film is removed from the optical test unit with said removable housing, wherein said at least one film is a filter, wherein said filter is one of: (i) an optical filter for preventing a second portion of light illuminating the aerosol sample from passing through said optical filter; and, (ii) an aerosol filter for preventing aerosol from passing through said aerosol filter.

7. The removable aerosol test chamber of claim 6, wherein:
   (a) said at least one film includes at least one of a horizontal depolarization filter, a vertical depolarization filter and a fluorescence filter.

8. The removable aerosol test chamber of claim 6, wherein:
   (a) said removable aerosol test chamber being configured such that when said removable aerosol test chamber is installed in an optical test unit in an operating position, said removable aerosol test chamber isolates an aerosol sample directed into said aerosol test chamber from at least one optical component of the optical test unit to prevent the at least one optical component from becoming contaminated by the aerosol sample.

9. The removable aerosol test chamber of claim 6, wherein:
   (a) said removable housing includes an aerosol nozzle extending downwardly from an upper portion of said removable housing and an aerosol outlet formed in a lowermost portion of said removable housing, wherein the aerosol outlet is configured to allow the aerosol sample to pass out of the aerosol test chamber.

10. The removable aerosol test chamber of claim 6, wherein:
    (a) said removable housing further includes a film sealing said light inlet.

11. The removable aerosol test chamber of claim 10, wherein:
    (a) said film sealing said light inlet is a filter.

12. The removable aerosol test chamber of claim 11, wherein:
    (a) said filter is a horizontal polarization filter.

13. A removable aerosol test chamber configured to be inserted into and removed from an optical test unit having optical components including a light source for illuminating an aerosol sample directed into said removable aerosol test chamber and at least one detector for detecting at least one characteristic of light illuminating the aerosol sample directed into said removable aerosol test chamber, said removable aerosol test chamber comprising:
    (a) a removable housing having an aerosol test chamber, an aerosol inlet, a light inlet and a filter, said aerosol inlet of said removable housing being configured to introduce an aerosol sample into said aerosol test chamber, said light inlet being configured to direct light from a light source into said aerosol test chamber when said removable aerosol test chamber is installed in an optical test unit in an operating position; and,
    (b) said removable housing further including a particle collector for collecting particles from the aerosol sample passing into said aerosol test chamber such that upon removal of said removable housing from the optical test unit particles collected on the particle collector remain in said removable housing.

14. The removable aerosol test chamber of claim 13, further including:
    (a) means for sealing said aerosol test chamber such that when said removable aerosol test chamber is inserted in an operating position in an optical test unit, said aerosol test chamber is substantially sealed to prevent an aerosol sample passing into said aerosol test chamber from contaminating one or more optical components of the optical test unit.

15. An apparatus for testing an aerosol sample, said apparatus comprising:
    (a) an optical test unit including one or more optical components including at least one of a laser light source for illuminating an aerosol sample and at least one detector for detecting at least one characteristic of light illuminating the aerosol sample, said optical test unit having a housing for housing the one or more optical components, said housing having an exterior surface;
    (b) a first removable cartridge removably connected to said optical test unit, said first removable cartridge forming a sealed aerosol test chamber to isolate an aerosol sample passing into said sealed aerosol test chamber from at least one optical component of the optical test unit to prevent the at least one optical component from becoming contaminated by the aerosol sample, said first removable cartridge having a removable filter, said removable filter being disposed inwardly from said exterior surface of said housing of said optical test unit so that said removable filter does not form any portion of the exterior surface of said optical test unit.

16. The apparatus as set forth in claim 15, further including:
    (a) a second removable cartridge to be removably connected to said optical testing unit upon removal of said first removable cartridge, wherein said second removable cartridge having at least one film for sealing at least one opening in said second removable cartridge that affects light passing therethrough differently from the at least one film sealing at least one opening of said first removable cartridge.

17. The apparatus as set forth in claim 15, wherein:
    (a) said first removable cartridge includes a light trap.

18. A removable insert configured to be inserted into and removed from a test unit having a light source for illuminating an aerosol sample directed into an aerosol test chamber and at least one detector for detecting at least one characteristic of light illuminating the aerosol sample directed into the aerosol test chamber, said removable insert comprising:
 (a) a removable support configured to be inserted into and removed from the test unit; and,
 (b) said removable insert further including each of the following:
  (i) at least one filter, said at least one filter being connected to said removable support such that said at least one filter is removed from the test unit with said removable support, said at least one filter being disposed such that at least a first portion of light from the light source will pass through said at least one filter before the first portion of light is detected by at least one detector of the test unit; and,
  (ii) a particle collection means for collecting particles from the aerosol sample, said particle collection means being operably associated with the removable support such that particles collected by said particle collection means are removed from the test unit upon removal of the removable support from the test unit.

19. The removable insert as set forth in claim 1, wherein:
(a) said removable insert includes a cover for sealing an opening formed in an exterior surface of said housing of said optical test unit, said exterior surface is substantially planar and said cover is larger than said opening formed in said exterior surface of said housing of said optical test unit.

\* \* \* \* \*